United States Patent [19]

Pauzat et al.

[11] Patent Number: 4,969,095
[45] Date of Patent: Nov. 6, 1990

[54] SCINTILLATION CAMERA HAVING COMPUTER CONTROL OF ELECTRICAL SIGNALS INDICATING SCINTILLATIONS

[75] Inventors: Vincent Pauzat, Montgeron; Michel R. Jatteau, Paris, both of France

[73] Assignee: U.S. Philips Corporation, New York, N.Y.

[21] Appl. No.: 141,353

[22] Filed: Jan. 6, 1988

[30] Foreign Application Priority Data

Oct. 6, 1987 [FR] France ................ 87 00042

[51] Int. Cl.$^5$ ............................ G06F 15/42
[52] U.S. Cl. ................ 364/413.26; 378/901; 364/413.13
[58] Field of Search ............ 364/413.13, 413.24, 364/413.26

[56] References Cited

U.S. PATENT DOCUMENTS

| | | | |
|---|---|---|---|
| 4,468,744 | 8/1984 | Kakegawa | 364/413.26 |
| 4,546,255 | 10/1985 | Knoll | 364/413.24 |
| 4,652,760 | 3/1987 | Kondo | 364/413.24 |
| 4,661,909 | 4/1987 | Kumazawa | 364/413.24 |
| 4,769,755 | 9/1988 | Yamakawa | 364/413.24 |

Primary Examiner—Allen MacDonald
Assistant Examiner—Gail O. Hayes
Attorney, Agent, or Firm—Paul R. Miller

[57] ABSTRACT

Scintillation camera inlcuding a scintillator crystal, a light guide, a set of p photodetectors, p acquisition channels (60), and a computer (100) intended to deliver the coordinates $x_j$ and $y_j$ of a scintillation j and the energy $E_j$ which is associated with this event j. This camera is characterized in that there is provided, between the output of the p acquisition channels and the input of the computer, a transfer control stage (200) including: (a) p subtractors (180) receiving on a first input the corresponding output of the p acquisition channels (60) and on a second common input a so-called slaved threshold evaluated by a threshold computer (170), (b) an additional acquisition channel (160) supplying to the threshold computer the digital energy signal $E_{mj}$, (c) at the output of the additional acquisition channel and of the p substractors, (p+1) transfer control circuit (190), the $(p+1)^{th}$ of these circuits providing the energy transfer signal, and (d) a transfer bus (250) receiving the (p+1) output signals of the (p+1) transfer control circuits and delivering to the computer (100) on the one hand the energy signal and on the other hand p' signals from among the p output signals of the p first transfer control circuits.

15 Claims, 7 Drawing Sheets

SCINTILLATION CAMERA HAVING COMPUTER CONTROL OF ELECTRICAL SIGNALS INDICATING SCINTILLATIONS

The present invention relates to a scintillation camera including a scintillator crystal, a matrix of p photodetectors with each of which is associated, after conversion of each scintillation into an electrical value, a respective output signal received by p acquisition channels themselves delivering p electrical signals of characteristics linked in particular with the intensity of the scintillation and with the distance of this scintillation from each of the photodetectors, and a computer intended to deliver the coordinates $x_j$ and $y_j$ of a scintillation j and the energy $E_j$ which is associated with this event j.

BACKGROUND OF THE INVENTION

In order to determine the radioactive fixations image inside an organ, medicine makes use, among other means, of the principle of scintigraphy. This principle consists in introducing into the organism of a patient a radioactive element which will be more or less fixed on certain organs depending on whether these are healthy or unhealthy. The measurement of the intensity of emitted gamma radiation then provides an indication of the distribution of the radioactive element in the organism and therefore constitutes a radioactive aid. Such a measurement is carried out using a scintillation camera.

In conventional scintillation cameras, for example the Anger type camera (see U.S. Pat. No. 3,011,057), the gamma rays representing the radioactive distribution in the examined environment penetrate, after passing through a collimator, into a scintillator crystal. The scintillations which occur in the crystal are then detected by means of a whole series of photomultiplier tubes (for example 19, 37, etc. . . . ), after passing through a light guide providing optical coupling between the crystal and the tubes. These tubes are distributed in front of the optical unit (crystal +light guide) in order to practically cover its entire surface and to transform the light energy of each appearing scintillation into a measurable electrical signal.

With each photomultiplier tube there is then associated an analog acquisition channel successively carrying out an amplification, an integration and a shaping of the signals provided by the tube. The outputs $S_{ij}$ of the assembly of acquisition channels are sent to a computer which provides, by estimation, the coordinates $x_j$ and $y_j$ of a scintillation j and its energy $E_j$, the index i indicating which of the acquisition channels is concerned. In the computer, several types of computing device can be provided, but essentially two of them are actually used, namely an arithmetic ratio barycentric computing device, or a logarithmic ratio barycentric computing device. In an arithmetic ratio barycentric computing device, the values $x_j$, $y_j$ and $E_j$ are given by the equations:

$$x_j = \frac{X_j}{Z_j} \tag{1}$$

$$y_j = \frac{Y_j}{Z_j} \tag{2}$$

$$E_j = \sum_{i=1}^{i=p} G_i S_{ij} \tag{3}$$

In these expressions, we have:

$$X_j = \sum_{i=1}^{i=p} K_i S_{ij} \tag{4}$$

$$Y_j = \sum_{i=1}^{i=p} H_i S_{ij} \tag{5}$$

$$Z_j = \sum_{i=1}^{i=p} J_i S_{ij} \tag{6}$$

with the coefficients $G_i$, $K_i$, $H_i$, $J_i$ being weighting factors associated with the position of the axis of each of the p photomultiplier tubes.

In a logarithmic ratio barycentric computing device, the values $x_j$, $y_j$, $E_j$ are this time given by the equations:

$$x_j = \frac{1}{a} \text{Log} \frac{X_j^+}{X_j^-} \tag{7}$$

$$y_j = \frac{1}{a} \text{Log} \frac{Y_j^+}{Y_j^-} \tag{8}$$

$$E_j = \sum_{i=1}^{i=p} G_i S_{ij} \tag{9}$$

with:

$$X_j^+ = \sum_{i=1}^{i=p} K_i^+ S_{ij} \tag{10}$$

$$X_j^- = \sum_{i=1}^{i=p} K_i^- S_{ij} \tag{11}$$

$$Y_j^+ = \sum_{i=1}^{i=p} H_i^+ S_{ij} \tag{12}$$

$$Y_j^- = \sum_{i=1}^{i=p} H_i^- S_{ij} \tag{13}$$

in which the weighting factors are similarly associated with the position of the axis of each of the p photomultiplier tubes.

In the rest of the description it will be considered, without this being a limitation of the invention described later, that there is used for example an arithmetic ratio barycentric computing device.

The transfer of the output signals of the p acquisition channels to the computer determining the coordinates and the energy of the events j is very different according to whether these signals are analog, as in most of the conventional cameras, or digital, as in certain scintillation cameras of more recent design in which an analog-digital conversion of the signals is carried out in the acquisition channels.

When the output signals are analog, their transfer is carried out by means of resistor networks, whose ohmic value is proportional to the weighting factors, and summing amplifiers. An example of this type of signals transfer is described in the French Patent application, No. FR-A-2,288,987. According to this document, the objective of the described camera is to remedy the disadvantage which consists in using the output signals of all of the photodetectors for the localization of the scintillations. For this purpose, the camera includes means for selecting, from all of the output signals, a predetermined fixed number (three in the proposed example) of them, those of the photodetectors whose output signals are affected by a mediocre signal-to-noise ratio thus being eliminated. Because of this, the spatial resolution of the camera is improved.

Such a measure does not, however, enable in any way an improvement in the maximum counting of the camera. The applicant companies have in effect stated the limitations of the prior productions in terms of speed, particularly when the events to be detected are very close and when the scintillations, also very close in time, lead to at least a partial stacking of the electrical pulses corresponding to them.

SUMMARY OF THE INVENTION

The object of the invention is to propose a scintillation camera which is substantially faster than the prior productions, particularly in the mentioned situation of the stacking of signals corresponding to scintillations.

For this purpose the camera according to the invention is characterised:

(A) in that the p acquisition channels carry out the amplification, filtering and sampling of the output signals of the photodetectors, then the analog-digital conversion of the samples obtained and their summing, and deliver p digital signals;

(B) in that there is provided, between the output of the p acquisition channels and the input of the computer, a transfer control stage, mainly intended to control, among the p available signals at the output of the channels, the transfer to the computer of a random number p' of these signals, this number p' being selected by the computation of a threshold $m_{oj}$ slaved both to the energy and to the stacking effect of the detected events and elimination of the p-p' signals lower than the said slaved threshold;

(C) in that the computer itself includes:

(a) a digital summing stage receiving the output signals from the transfer control stage and principally delivering the following signals $X_{m,j}$, $Y_{m,j}$, $Z_{m,j}$:

$$X_{m,j} = \sum_{i=1}^{i=p'} K_i (M_{ij} - m_{oj})$$

$$Y_{m,j} = \sum_{i=1}^{i=p'} H_i (M_{ij} - m_{oj})$$

$$Z_{m,j} = \sum_{i=1}^{i=p'} J_i (M_{ij} - m_{oj})$$

as well as the digital energy signal $K_{m,j}$, with $K_i$, $H_i$, $J_i$ being weighting coefficients;

(b) an event processing stage receiving the signals $X_{m,j}$, $Y_{m,j}$, $Z_{m,j}$, $E_{m,j}$ and delivering three of the coordinates and energy signals x, y E;

(D) in that a detection, sequencing and storage stage, receiving from a summing amplifier an analog signal which corresponds with the sum of the p output signals of the photodetectors, is provided for delivering on the one hand the various clock signals for the synchronization of the p acquisition channels, from the transfer control stage, and from the computer and, on the other hand, correction coefficients intended for the event processing stage;

(E) in that the transfer control stage itself includes:

(a) p subtractors receiving on the one hand on a first input the corresponding output of the p acquisition channels and, on the other hand, on a second common input the slaved threshold evaluated by a threshold computer;

(b) an additional acquisition channel providing to the threshold computer the digital energy signal $E_{m,j}$ for the evaluation of the slaved threshold;

(c) at the output of the additional acquisition channel and of the p subtractors, (p+1) transfer control circuits, the $(p+1)^{th}$ of these circuits providing the transfer of the energy signal;

(d) a transfer bus receiving the (p+1) output signals of the (p+1) transfer control circuits and delivering to the computer on the one hand the energy signal and on the other hand p' signals from among the p output signals of the p first transfer control circuits.

In a variant embodiment of the camera thus proposed, the computer can use the value E instead of the value Z for the computation of the coordinates, taking account of the possibilities of subsequent correction offered by currently available gamma cameras. In this case the computer includes only two digital weighted summing devices. The digital summing stage variant thus constituted delivers the following signals $X_{m,j}$, $Y_{m,j}$ ($K_i$ and $H_i$ being weighting coefficients):

$$X_{m,j} = \sum_{i=1}^{i=p} K_i (M_{ij} - m_{oj})$$

$$Y_{m,j} = \sum_{i=1}^{i=p} H_i (M_{ij} - m_{oj})$$

and the previously determined signal $E_{m,j}$.

These signals are provided either directly at the output of the first and second digital weighted summing devices, for the first two of these signals, or by means of a time realignment circuit provided at the output of the last device, for the last of these signals.

In one or other of these camera structures, a considerable gain in signal transfer speed is obtained, which enables a maximum counting rate to be achieved which is considerably greater than that of the best performing currently available cameras.

BRIEF DESCRIPTION OF THE DRAWINGS

Other features and advantages of the invention will now appear in the following description and in the appended drawings, given by way of non-limiting examples and in which.

DESCRIPTION OF THE INVENTION

In scintillation cameras provided with p acquisition channels using converter-integrator circuits such as the device described in the French patent application FR-A-2,540,995 or that described in the French patent FR-A-2,552,233, the signals obtained at the output of the acquisition channels are a measurement of the charge of the electrical pulses provided by the respective photomultiplier tubes in response to a scintillation.

For example, in the absence of any stacking effect, the acquisition channel i (i varying from 1 to p) would provide a signal $S_{ij}$ in response to a scintillation j occurring at a point $x_j$, $y_j$ of the scintillator crystal. If, on the other hand, there is a stacking of events as shown by way of example in FIG. 1a which shows individual signals corresponding to close scintillations giving rise to a partial stacking, the signal $M_{ij}$, provided by the acquisition channel i for an event j and measured at the end of the time interval $\theta_{j,j+1} = t_{o,j+1} - t_{o,j}$ during which this event j is only disturbed by the previous events, is no longer $S_{ij}$ but a signal depending on $S_{ij}$ and the values $S_{ik}$ (k = j−1, j−2, ..., j−q+1, j−q) corresponding to the q previous events which participate in the disturbances of the event j.

More precisely, it can be shown that, for each of the acquisition channels, the measured signal $M_{ij}$ has the following theoretical form:

$$m_{ij} = \frac{S_{ij}}{\alpha_j} + \sum_{k=j-1}^{k=j-q} \gamma_{kj} S_{ik} \quad (14)$$

In this equation (14), the coefficients $\alpha_j$ and $\gamma_{kj}$ are correction coefficients, predetermined from knowledge of the average shape, as a function of time, of the analog pulses provided at the input of the acquisition channels. The coefficients $\alpha_j$, obtained by extrapolation, depend only on the time interval $\theta_{j,j+1}$ of the measurement. These coefficients $\alpha_j$, greater than 1, would therefore tend towards the value 1 if the duration of the measuring interval $\theta_{j,j+1}$ became very large. The coefficients $\gamma_{kj}$, obtained by interpolation, depend on the time interval $\theta_{kj}$ separating each previous event j−1, j−2, etc... of the event j and expressed by the equation $\theta_{kj} = t_{o,j} - t_{o,k}$ with k = j−1, j−2, ..., q−1, q. These coefficients $\gamma_{kj}$, less than 1, would tend towards the value 0 if the duration of the intervals $\theta_{kj}$ became very large.

Figure 1:
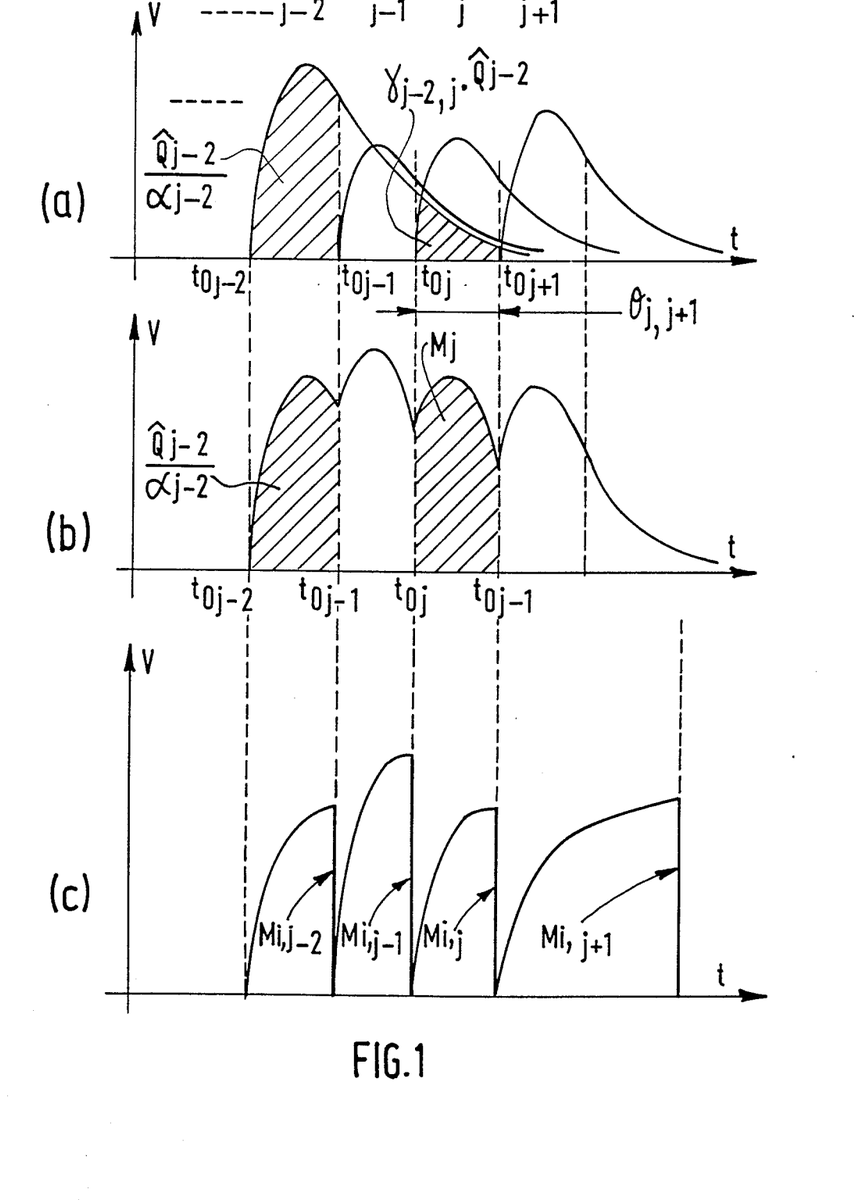
FIGS. 1a to 1c respectively show the shape of the individual signals corresponding to close scintillations giving rise to a partial stacking (FIG. 1a), the shape of the overall signal resulting from this stacking (FIG. 1b), and the shape of the signal representing for each event j the measured value at the time $t_{o,j+1}$ and which results from the summing of the samples during the time interval $\theta_{j,j+1}$ for the acquisition channel i (FIG. 1c)

In FIG. 1a, the electrical charge to be determined, which would be referenced $\hat{Q}_j$ and which is proportional to the quantity of current delivered during the duration $\theta_{j,j+1}$ of the individual signal associated with the event j is estimated from the measurement $M_{ij}$ carried out during this period and starting from the q charges $\hat{Q}_k$ previously estimated. FIG. 1b shows the sum signal, or composite signal, resulting from the stacking of the individual signals (of FIG. 1a) corresponding with several scintillations which are close in time. FIG. 1c shows the waveform of $M_{i,j}$ [sic] successive signals.

For the evaluation of the coordinates $x_j$, $y_j$ of each event j by the computer from the signals provided by the p acquisition channels, and to do this in a way which is independent of the fact that there is or is not a stacking of events, a threshold reference $m_{oj}$ which is variable from one event to another is introduced.

In this way, the computer carries out in an initial time the following weighted sums:

$$X_{m,j} = \sum_{i=1}^{i=p} K_i (M_{ij} - m_{oj}) \quad (15)$$

$$Y_{m,j} = \sum_{i=1}^{i=p} H_i (M_{ij} - m_{oj}) \quad (16)$$

$$Z_{m,j} = \sum_{i=1}^{i=p} J_i (M_{ij} - m_{oj}) \quad (17)$$

with $M_{ij} - m_{oj} = 0$ if $M_{ij}$ is less than or equal to $m_{oj}$. In these equations (15) to (17), the weighting factors are for example the same as before.

It can be shown that the value of the threshold $m_{oj}$ is advantageously, without this of course being the only possible choice, taken as proportional to the value $E_{mj}$. The proportionality factor is called $f_o$ and is expressed as V/eV if $m_{oj}$ is a voltage and if $E_{mj}$ is expressed in electron volts, and we therefore have:

$$m_{oi} = f_o \cdot E_{mj} \quad (18)$$

In this type of camera, the digital signal $E_{mj}$ results from the sampling, the digitization and the digital integration of the analog weighted sum obtained at the output of the analog summing-amplifier. If there had been no stacking, this amplifier would provide a signal proportional to the energy $E_j$ of each of the events. When there is stacking of events, $E_{mj}$ is expressed according to the equation (14), as a function of the energy $E_j$ of the event j and that of the previous q events, $E_k$, according to the following equation:

$$E_{mj} = \frac{E_j}{\alpha_j} + \sum_{k=j-1}^{k=j-q} \gamma_k \cdot E_k \quad (19)$$

which gives, by replacing in $m_o = f_o \cdot E_{mj}$:

$$m_{oj} = f_o \cdot \left( \frac{E_j}{\alpha_j} + \sum_{k=j-1}^{k=j-q} \gamma_{kj} \cdot E_k \right) \quad (20)$$

expressions in which k varies from j−1 to j−q.

In practice, the applicant has observed that only a certain number p' of signals $M_{ij} - m_{oj}$ are truly useful for computing the weighted sums $X_{mj}$, $Y_{mj}$, $Z_{mj}$. This situation results from the fact that the photomultiplier tubes located at a large distance from the point of scintillation receive a very low quantity of light, for which the signal at the output of the corresponding acquisition channels is less than the threshold $m_{oj}$. A large distance is understood, for example to be a distance in the order of two times greater than that which separates the axes of two adjacent tubes.

The number p' of signals $M_{ij} - m_{oj}$ to be transferred, for each scintillation, to the computer can therefore, in reality, be less than p. This number p' essentially depends on the one hand on the construction of the optical unit (crystal + light guide) of the viewing head of the scintillation camera and on the other hand on the value of the threshold $m_{oj}$ (i.e. of the factor $f_o$ of proportionality of the energy $E_{mj}$ of the events, a factor which is preset when testing the camera in order to obtain the best possible spatial resolution). The number p' is, in practice, for example between 9 and 15, taking account of statistical fluctuations, in high spatial resolution cameras, and p' = 12 can be taken as average.

It has previously been seen that the duration of transfer of signals was equal to p.Δt. In a scintillation camera including for example 61 photomultiplier tubes and therefore p =61 acquisition channels, the transfer duration is no longer equal to 61Δt but on average to p'.Δt =12Δt in the case of this example. The gain in transfer speed and consequently in the maximum counting rate is, in this case, in the order of 5. In general, this gain is given by the value of the ratio p/p'.

The implementation of the invention can be envisaged in different embodiments which will be described in succession, in a detailed way in a first embodiment and only in their variants for the subsequent embodiments.

Figure 2:
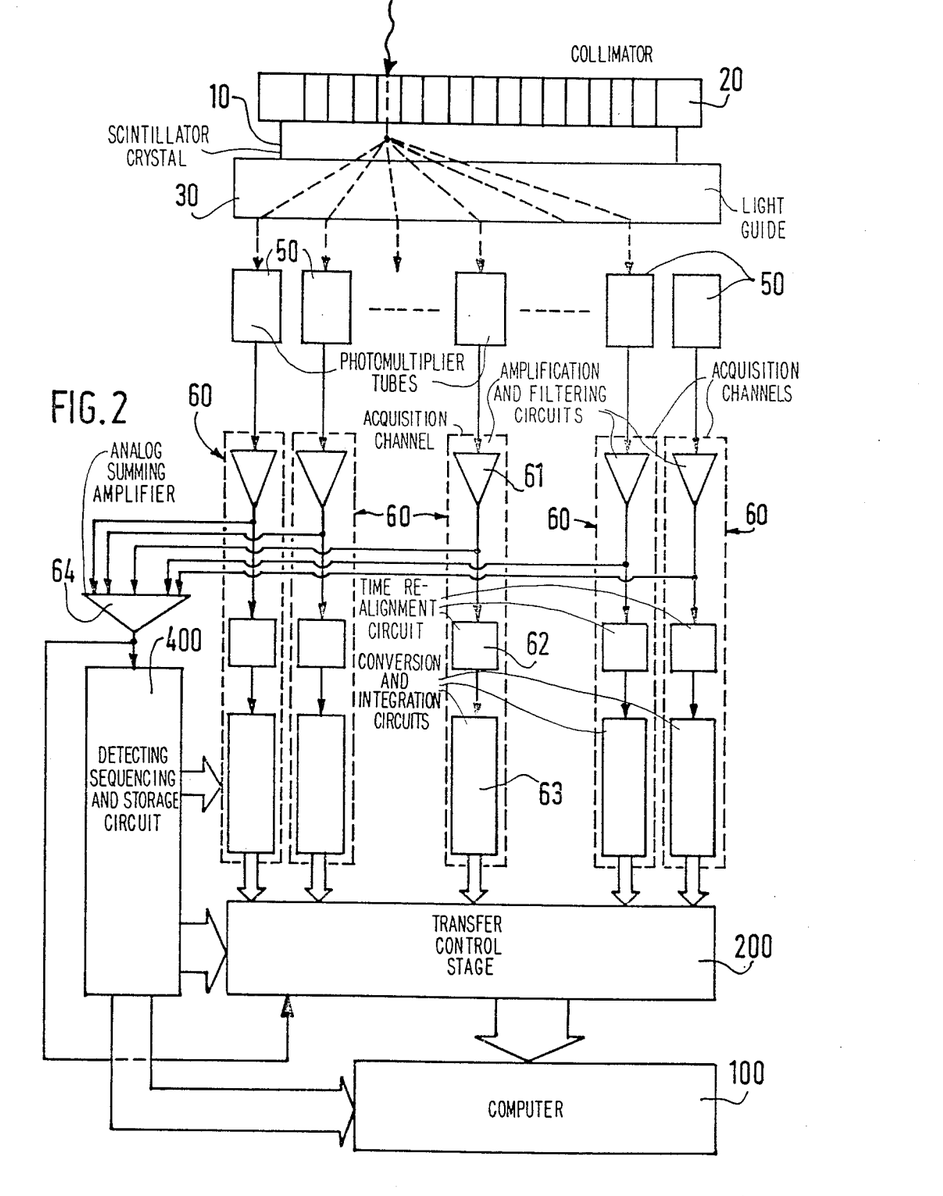
FIG. 2 shows the block diagram of a scintillation camera according to the invention.

In the first embodiment, shown in FIG. 2, the scintillation camera according to the invention includes a scintillator crystal 10 fitted with a collimator 20 and intended to convert each photon received into a scintillation. This crystal is coupled by means of a light guide 30 to the input window of a set of p photo-detectors here constituted by photomultiplier tubes 50. These tubes 50 convert each scintillation into a current which is then processed by p acquisition channels 60. These acquisition channels 60 successively carry out the amplification, filtering and sampling of the output signals of the photomultiplier tubes 50 and then the analog-digital conversion of the samples obtained and the summing of these digital samples. The value of these p digital signals is tied to that of the output current of the tubes 50 and therefore with a fraction of the intensity of the initial scintillation, but differently depending on the stacking rate of the scintillations (this fraction is itself tied to the production of the optical block and in particular to the distance between the point of scintillation and the axis of the tubes). If there was no stacking, the value of each of these signals would be referenced $S_{i,j}$; the estimation of these values in the presence of stacking would be referenced $S_{i,j}$.

Each of these p channels includes for example, in series, in order to carry out the above mentioned functions, an amplification and filtering circuit 61 receiving the output of the corresponding tube 50, a time realignment circuit 62, then a conversion and integration device 63 successively providing the sampling of the output signals of the corresponding circuit 62, the analog-digital conversion of the samples obtained and the summation of these.

Figure 3:
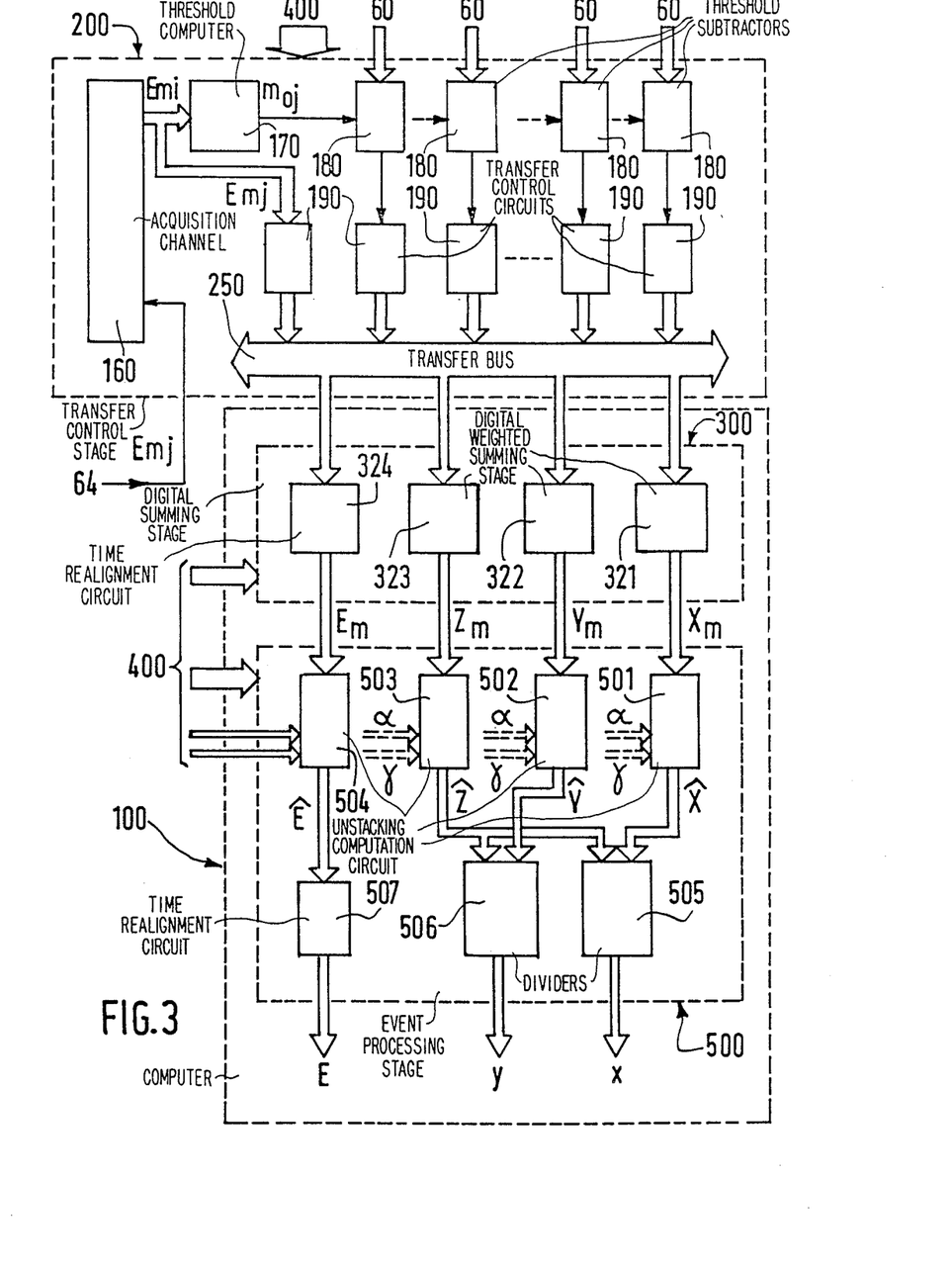
FIG. 3 shows an embodiment of the transfer control stage and of the computer of the camera in FIG. 2.

An analog summing amplifier 64 receives on p inputs the p analog outputs of the amplification and filtering circuit 61 of the p channels 60, and the output of this summing amplifier 64 is connected to the input of a detection, sequencing and storage stage 400 which will be described later. This output of the amplifier 64 is also connected, as can be seen in FIG. 3, to the input of a $(p+1)^{th}$ acquisition channel 160, which includes the same elements 61 to 63 as the first p channels 60. This additional acquisition channel 160 provides a digital signal $E_{mj}$ which is sent on the one hand to a threshold computer 170 delivering at its output the value of the threshold $m_{oj}$ and, on the other hand, to a transfer control circuit 190. This threshold $m_{oj}$ is supplied to p threshold subtractors 180 placed in series with the p acquisition channels 60. These subtractors 180 respectively deliver on their output either a zero signal if $M_{ij}-m_{oj}$ is less than or equal to 0, or the value $M_{ij}-m_{oj}$ if this value is positive.

Transfer control circuits 190 are provided on the one hand in series with the p subtractors 180 respectively and therefore with the corresponding p acquisition channels 60, and, on the other hand, at the output of the additional acquisition channel 160. It is these control circuits 190 which will enable, under the control of the stage 400, to transfer to the computer 100 only p' signals instead of all of the p available signals at the output of the p acquisition channels 60, as well as the signal $E_{mj}$ at the output of the channel 160, by means of a transfer bus 250.

The assembly of the elements 160, 170, 180, 190 and 250 constitute the transfer control stage 200. It would of course be equivalent, as regards the structure of the invention, if the bus 250 were not considered as included in this stage 200, but rather in the computer 100 which is now described. It would also be possible to transfer, over a separate line of the bus, the digital signal $E_{mj}$ of the output of the acquisition channel 160 to the input of the computer 100. Finally, it is also equivalent to envisage that the p elements 180 and 190 associated with each of the p acquisition channels are included in these channels. The transfer sequence of the data $(M_{ij}-m_{oj})$ on the bus 250 can then be managed by a protocol known under the English name "Daisy-chain".

The computer 100, shown in FIG. 3 in the case of an arithmetic ratio barycentric computing device, is arranged as follows. It includes firstly a digital summing stage 300, itself composed of three digital weighted summing devices 321, 322, 323, and a time realignment circuit 324 of the digital signal $E_{mj}$. These devices respectively carry out the following weighted summations:

$$X_{m,j} = \sum_{i=1}^{i=p'} K_i (M_{ij} - m_{oj}) \quad (21)$$

$$Y_{m,j} = \sum_{i=1}^{i=p'} H_i (M_{ij} - m_{oj}) \quad (22)$$

$$Z_{m,j} = \sum_{i=1}^{i=p'} J_i (M_{ij} - m_{oj}) \quad (23)$$

which are similar to the summations defined by the equations (15) to (17) but relate only to p' signals instead of p. Each of these three digital weighted summation devices is for example of the TDC 1009 multiplier-accumulator type marketed by the TRW Corporation, La Jolla, CA 92 038, USA, one of whose inputs receives the output $M_{ij}-m_{oj}$ and whose other input receives the weighting coefficients in digital form, stored in an auxiliary memory. In the case in which this type of multiplier-accumulator is effectively used, the auxiliary memory, which must be synchronized with the overall operating of the computer, can for example be built into the detection, sequencing and storage stage 400 described later.

The output signals $X_{mj}$, $Y_{mj}$, $Z_{mj}$, $E_{mj}$ available at the output of the digital summation stage 300 are then supplied to an event processing stage 500. This stage 500 includes, as shown in FIG. 3, four unstacking computation circuits 501 to 504, two dividers 505 and 506 and a time realignment circuit 507.

Figure 4:
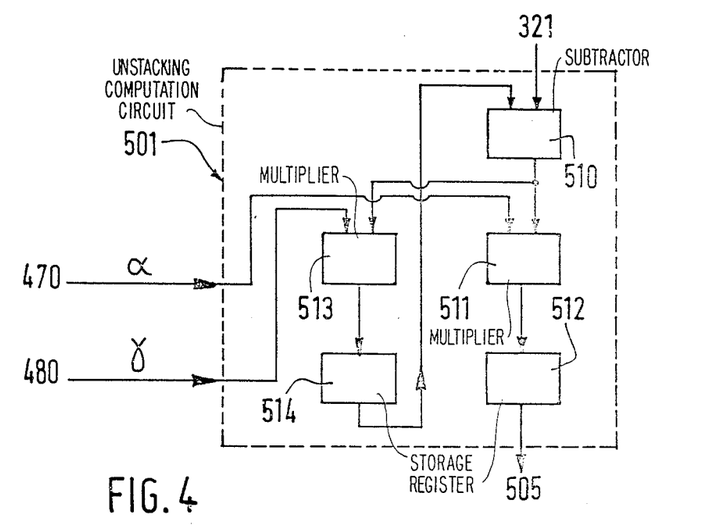
FIGS. 4 and 6 show two embodiments of unstacking computation circuits of the event processing stage.

As the four circuits 501 to 504 are identical, only one of them is described here, circuit 501 for example. This circuit, shown in FIG. 4, includes a subtractor 510 receiving on its first positive input the output of the corresponding digital weighted summation device 321 (circuits 501 to 504 correspond with the devices 321 to 324 respectively). The subtractor 510 is followed by a first multiplier 511 and a storage register 512 whose output is that of the circuit 501. The subtractor 510 is also followed, in parallel with the elements 511 and 512, by a second multiplier 513 and a second storage register 514. These multipliers can be replaced by a single multiplication circuit associated with a time multiplexer-demultiplexer. The negative input of the subtractor 510 is connected to the output of the storage register 514. The second input of the multiplier 511 is connected to the output of a memory 470 storing the coefficients $\alpha_j$ and that of the multiplier 513 is connected to the output of a memory 480 storing the coefficient $Y_{j,k}$. The outputs $\hat{X}, \hat{Y}, \hat{Z}, \hat{E}$ of the four unstacking computation circuits 501 to 504 are given, for the event j by the following equations:

$$\hat{X}_j = \alpha_j \left[ X_{m,j} - \sum_{k=j-1}^{k=j-q} \gamma_{k,j} \hat{X}_k \right] \quad (24)$$

$$\hat{Y}_j = \alpha_j \left[ Y_{m,j} - \sum_{k=j-1}^{k=j-q} \gamma_{k,j} \hat{Y}_k \right] \quad (25)$$

$$\hat{Z}_j = \alpha_j \left[ Z_{m,j} - \sum_{k=j-1}^{k=j-q} \gamma_{k,j} \hat{Z}_k \right] \quad (26)$$

$$\hat{E}_j = \alpha_j \left[ E_{m,j} - \sum_{k=j-1}^{k=j-q} \gamma_{k,j} \hat{E}_k \right] \quad (27)$$

The output $\hat{X}$ of the unstacking computation circuit 501 is sent to the first input of the divider 505 and the output $\hat{Y}$ of the circuit 502 to the first input of the divider 506. The second input of each of these dividers is constituted by the output $\hat{Z}$ of the unstacking computation circuit 503. The three outputs of the processing stage, which are also those of the computer, are constituted by the output $x_j = \hat{X}_j/\hat{Z}_j$ of the divider 505, the output $y_j = \hat{Y}_j/\hat{Z}_j$ of the divider 506 and the output $\hat{E}HD$ j of the time realignment circuit 507 provided at the output of the unstacking computation circuit 504.

Figure 5:
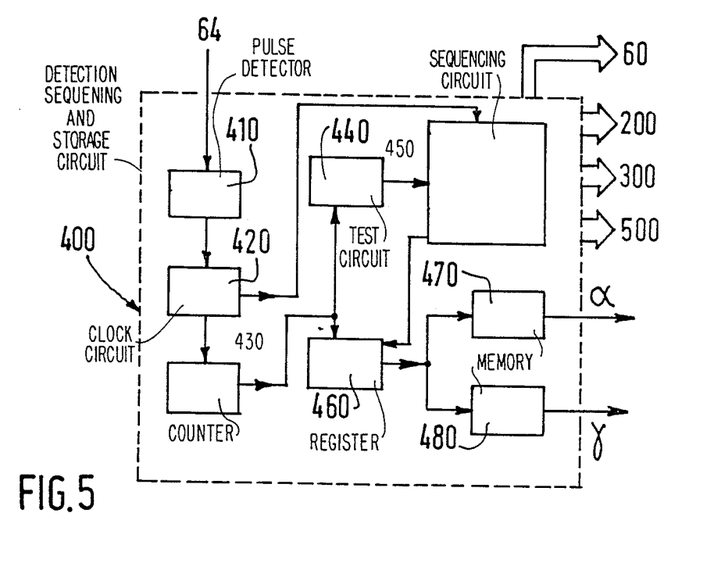
FIG. 5 shows an embodiment of the detection, sequencing and storage stage.

To these elements there is also associated the detection sequencing and storage stage 400. This stage 400, shown in FIG. 5, includes firstly a start of pulse detector 410, which receives the output of the analog summing amplifier 64 (see FIG. 2). This detector 410 is followed by a clock circuit 420 which generates periodic signals providing the control of a sequencing circuit 450 and that of a counter 430 of these clock signals. The number thus counted is submitted to a test circuit 440 whose output is sent to the sequencing circuit 450. This sequencing circuit 450 on the one hand provides the synchronization of the operations carried out in the acquisition channels and in the stages 200, 300 and 500, and, on the other hand, validates the contents of a register 460 for storing the output of the counter 430, a register which is in parallel with the test circuit 440. At the output of the register 460 are provided the two memories 470 and 480 mentioned above with reference to FIG. 4 and respectively storing the coefficients $\alpha_j$ and the coefficients $Y_{j,k}$.

In the first embodiment which has just been described, the proposed camera structure has enabled the derivation of the exact weighted sums $X_j$, $Y_j$, $Z_j$ of the values $\hat{X}_{m,j}$, $\hat{Y}_{m,j}$, $\hat{Z}_{m,j}$ and of the coefficients $\alpha_j$ and $Y_{k,j}$, by using the formulae (24) to (27).

In a second embodiment of the camera according to the invention, the determination, by the computer of the coordinates of the events can be carried out without introducing extrapolation, according to the following equations:

$$\hat{X}'_j = X_{m,j} - \sum_{k=j-1}^{k=j-q} \gamma_{k,j} X'_k \quad (28)$$

$$\hat{Y}'_j = Y_{m,j} - \sum_{k=j-1}^{k=j-q} \gamma_{k,j} Y'_k \quad (29)$$

$$\hat{Z}'_j = X_{m,j} - \sum_{k=j-1}^{k=j-q} \gamma_{k,j} Z'_k \quad (30)$$

still with $x_j = X'_j/Z'_j$ and $Y_j = Y'_j/Z'_j$. In this embodiment, the event processing stage is now referenced 600, and the three unstacking computation circuits which respectively receive the signals $X_m$, $Y_m$, $Z_m$ are, with reference to FIG. 4, modified by the removal of the multiplier 511.

Figure 6:
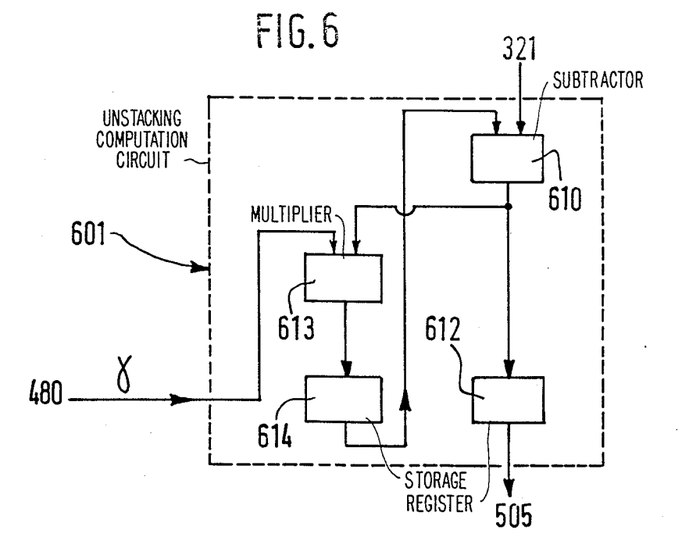

These three circuits in effect have the structure shown in FIG. 6 for any one of them, for example the first of these three circuits 601 to 603. This circuit 601 includes a subtractor 610 which receives on its first input the output of the corresponding digital weighted summation device 321. The subtractor 610 is followed on the one hand directly by a storage register 612, whose output is, as before, that of the unstacking computation circuit, and on the other hand, in parallel, by a multiplier 613 and then a storage register 614. The output of this register 614 is taken to the second input of the subtractor 610, and the other input of the multiplier 613 is connected to the output of the memory 480 provided in the stage 400 for the storage of the coefficient $\gamma$.

Figure 7:
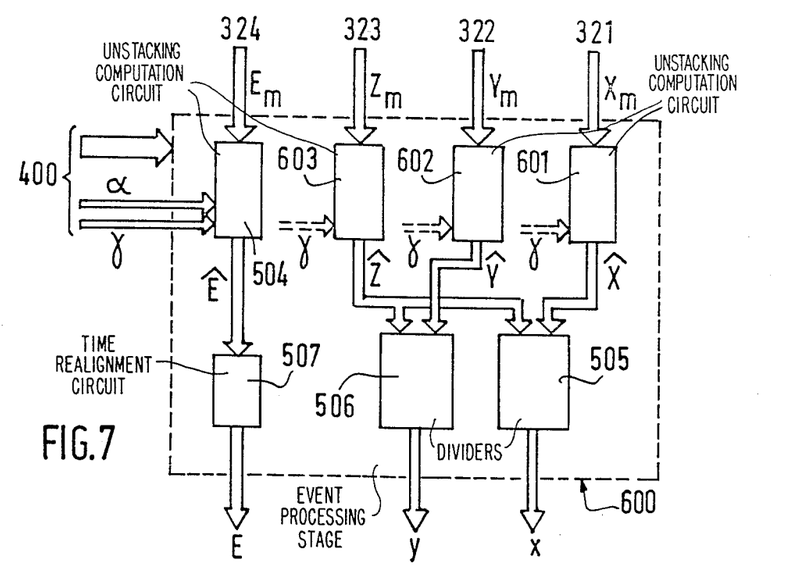
FIGS. 7 and 8 show two variant embodiments of the event processing stage of the computer shown in FIG. 3.

The other two circuits 602 and 603 include similar elements. The unstacking computation circuit 504 remains unchanged, the computer 100 now assumes the configuration shown in FIG. 7. The energy E is, as before, available at the output of the time realignment circuit 507.

In the second embodiment which has just been described, the structure of the computer has allowed the computation of the coordinates to be carried out as before, from the non-extrapolated weighted sums.

In a third embodiment of the camera according to the invention, another variant of the computer is proposed in which there is firstly determined the coordinates $x_{mj}$, $y_{mj}$, called measured coordinates, which are tainted with errors because of the stacking of events:

$$x_{mj} = X_{m,j}/Z_{m,j} \quad (31)$$

$$y_{mj} = Y_{m,j}/Z_{m,j} \quad (32)$$

After this determination the computation of the exact coordinates of the event j is then carried out by means of the following equations:

$$x_j = x_{m,j} - \sum_{k=j-1}^{k=j-q} \Gamma_{k,j} (x_k - x_{mj}) \quad (33)$$

$$y_j = y_{m,j} - \sum_{k=j-1}^{k=j-q} \Gamma_{k,j} (x_k - x_{mj}) \quad (34)$$

Figure 8:
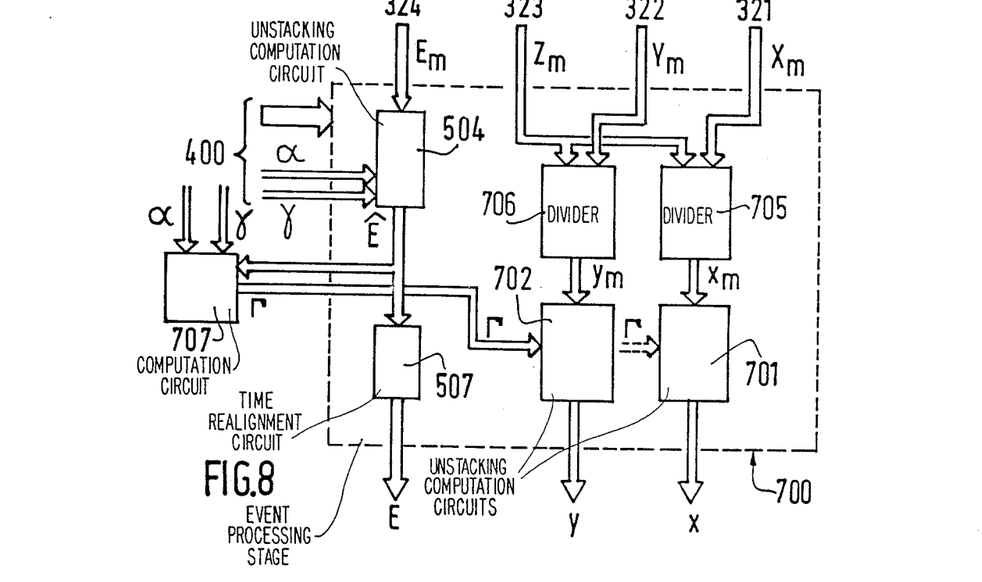

More precisely, in this third embodiment of the invention, the computer 100, shown this time in FIG. 8, includes a third type of event processing stage, referenced 700. In this variant embodiment of the computer, the unstacking is no longer carried out on the output signals $X_m$, $Y_m$, $Z_m$ of the digital summation stage 300 but on the coordinates $x_{mj}$ and $y_{mj}$ obtained at the output of the two dividers 705 and 706. The divider 705 receives the output signals $X_m$ and $Z_m$ of the digital summation stage 300, and the divider 706 receives the signals $Y_m$ and $Z_m$. The coordinates $x_j$, $y_j$ corresponding to the event j are then obtained at the output of the unstacking computation circuits 701 and 702, from, on the one hand, these so-called measured coordinates and, on the other hand, from the already known coordinates $x_k$, $y_k$ of the previous events which disturb the event j, according to the following equations (33) and (34).

The coefficients $\Gamma_{k,j}$, which are functions of the measured time intervals $\theta_{j,j+1}$, $\theta_{k,j}$ and of the ratios $\hat{E}_k/\hat{E}_j$ are computed in an additional computation circuit 707 which receives on the one hand the output E of the unstacking computation circuit 504, still present in the processing stage, and, on the other hand, the coefficients $\alpha$ and $\gamma$ delivered by the detection, sequencing and storage stage 400. In this example, the circuit 707 computes, on the one hand, from the successively received values of E, the successive ratios $\hat{E}_k/\hat{E}_j$ and, on the other hand, the products $\alpha_j \cdot \gamma_{k,j}$ from which are evaluated the coefficients $\Gamma_{k,j}$ according to the equation $\Gamma_{k,j} = \alpha_j \cdot \gamma_{k,j} \cdot \hat{E}_k/\hat{E}_j$. These coefficients $\Gamma_{kj}$ are supplied to the unstacking computation circuits 701 and 702, which have a configuration similar to that of the circuits 601 and 602. The energy E is, here again as before, available at the output of the time realignment circuit 507.

The present invention is, of course, not limited to the examples of embodiment described and shown, from which other variants can again be proposed without departing from the scope of the invention by so doing.

For example, an amplitude rejection circuit of the number of events to be processed can be provided in order to only carry out the computations on selected events (with the help of a threshold, an energy window, etc.) Also, a time multiplexer can be provided in order to use only one divider instead of two in each of the embodiments of FIGS. 3, 7 and 8. A time multiplexing circuit can also be provided in order to reduce the number of unstacking computation circuits and to use only a single unstacking computation circuit instead of the four circuits 501 to 504 in the case of the embodiment of FIG. 3, of the four circuits 601 to 603 and 504 in the case of the embodiment of FIG. 7, or of the three circuits 701, 702 and 504 in the case of the embodiment of FIG. 8. All of the variants proposed in this paragraph also apply to the other embodiments of FIGS. 9 to 11, mentioned below.

Taking account of the linearity and energy fault correction means which are implemented in currently available gamma cameras starting with the signals x, y, E obtained at the output of the computer, it is in fact known that it is possible to use either Z or E for the computation of the coordinates. In this case, it is possible to compute only one of these two values, the value E and to derive the other, Z, from computations applying the specific corrections of this choice and executed by the said means.

Figure 9:
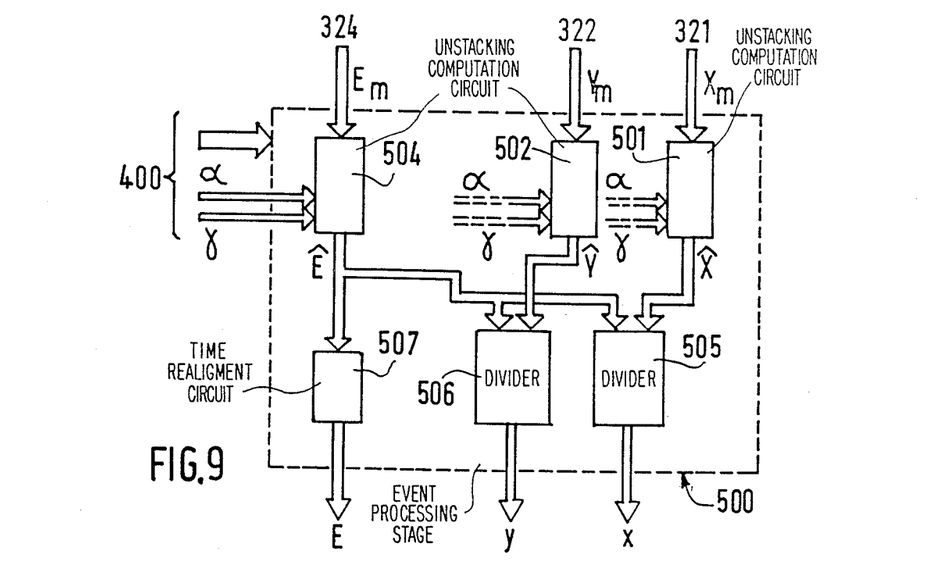
FIG. 9 to 11 show three other embodiments of the event processing stage.
Figure 10:
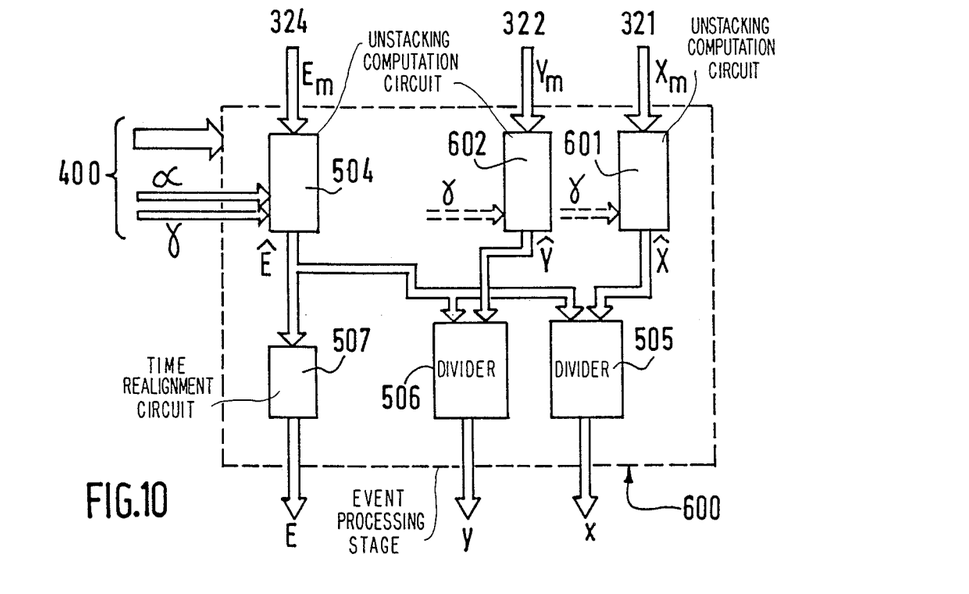
Figure 11:
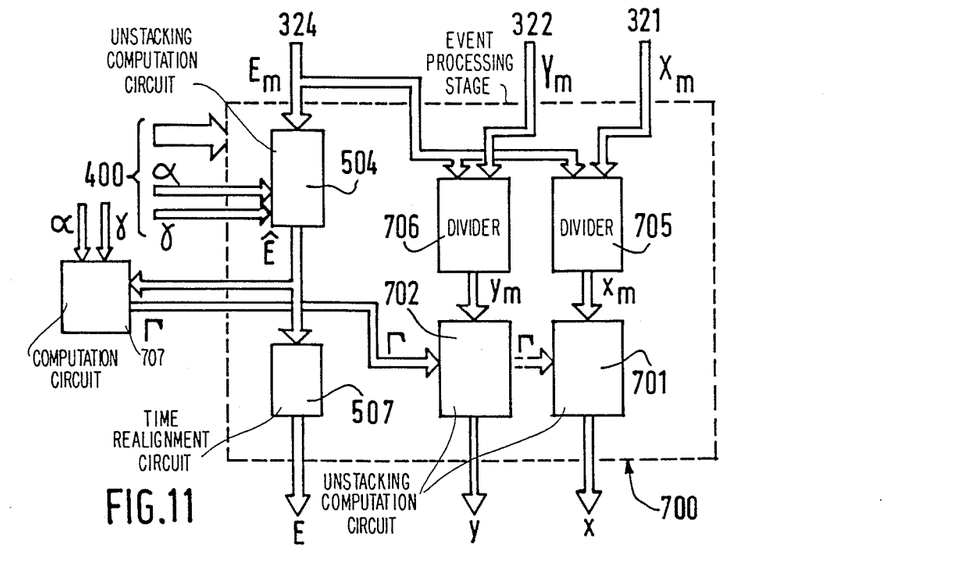

The digital summation stage 300 then only contains two digital weighted summing devices providing the signals $X_m$, $Y_m$, and similarly, the event processing stage 500 only includes three unstacking computation circuits. FIG. 9 to 11 show, in relation to FIGS. 3, 7 and 8 the modifications of the computer when only three channels X, Y, E are used.

In addition, it will also be noted that it is possible, in order to work at lower frequencies by regularizing the event rate, to introduce downstream of the p acquisition channels or upstream of the digital summation stage read and write FIFO memories controlled by the detection, sequencing and storage stage 400.

Finally, it is equivalent to consider that the bus 250 is incorporated in the computer, of which it is the input or access component, or, on the other hand, it is associated with it without being included in it.

What is claimed is:

1. Scintillation camera comprising a scintillator crystal, a matrix of p photodetectors, each providing a respective output signal after conversion of each scintillation into an electrical value, p acquisition channels delivering p electrical signals of characteristics of the intensity of the scintillation and of the distance of said scintillation from each of said photo-detectors, and computer means for delivering the coordinates $x_j$ and $y_j$ of a scintillation j and the energy $E_j$ associated with this event j, said scintillation camera further comprising (A) said p acquisition channels including means for amplifying, filtering and sampling said output signals of the photodetectors, and means for analog-digital converting and summing, of signals obtained, and said p acquisition channels delivering p digital signals, (B) transfer control stage means for connecting outputs of said p acquisition channels with said computer means and including means between the output of the p acquisition channels and the inputs of said computer means for controlling among the p available signals at the output of said channels the transfer to said computer means of a random number p' of said output signals, said number p' being selected by computation of a threshold $m_{oj}$ related both to the energy and to the stacking effect of detected events, said transfer control stage means eliminating p-p' signals lower than said threshold;

(C) said computer means further including:

(a) digital summing stage means for receiving said output signals from said transfer control stage means and for delivering signals $X_{m,j}$, $Y_{m,j}$, $Z_{m,j}$, where $$X_{m,j} = \sum_{i=1}^{i=p'} K_i (M_{ij} - m_{oj})$$

$$Y_{m,j} = \sum_{i=1}^{i=p'} H_i (M_{ij} - m_{oj})$$

$$Z_{m,j} = \sum_{i=1}^{i=p'} J_i (M_{ij} - m_{oj}),$$

and the digital energy signal $E_{mj}$, where $K_i$, $H_i$, $J_i$ are weighting coefficients;

(b) event processing stage means for receiving said signals $X_{m,j}$, $Y_{m,j}$, $Z_{m,j}$, $E_{m,j}$, and for delivering three coordinate and energy signals x, y, and E;

(D) detection, sequencing and storage stage means for receiving an analog signal from a summing amplifier, said analog signal corresponding with the sum of the p output signals of the photodetectors, said detection sequencing and storage stage means delivering various clock signals for synchronization of said p acquisition channels from said transfer control stage means and from said computer means, and said detection, sequencing and storage stage means delivering correction coefficients intended for said event processing stage means; and (E) said transfer control stage means further including:
(a) p subtractors receiving on a first input a corresponding output of the p acquisition channels and on a second common input said threshold evaluated by a threshold computer;
(b) an additional acquisition channel providing to said threshold computer said digital energy signal $E_{m,j}$ for evaluation of said threshold;
(c) (p+1) transfer control circuits located at the output of said additional acquisition channels and at said p subtractors, the $(p+1)^{th}$ of these circuits providing transfer of the energy signal; and
(d) transfer bus means for receiving the (p+1) output signals of said (p+1) transfer control circuits and for delivering to said computer means the energy signal and p' signals from among said p output signals of the p first transfer control circuits.

2. Scintillation camera according to claim 1, wherein said event processing stage means includes four unstacking computation circuit means for respectively receiving said digital signals $X_{m,j}$, $Y_{m,j}$, $Z_{m,j}$, $E_{m,j}$ and delivering four signals X, Y, Z, E, and two divider means for respectively delivering two signals $x = X/Z$ and $y = Y/Z$, said three signals x, y and E being respectively constituted by said output signals of each of said first divider means, said second divider means, and a time realignment circuit receiving means for receiving the output of a fourth one of said four unstacking computation circuit means, and wherein said correction coefficients are coefficients for correction by extrapolation and interpolation, $\alpha$ and $\gamma$ respectively, said coefficients being intended for said for unstacking computation circuit means.

3. Scintillation camera according to claim 2, wherein each of three of said unstacking computation circuit means includes a subtractor receiving on a first input a corresponding output of the digital summation stage means, followed by a storage register having an output of the unstacking computation circuit and a multiplier in parallel, and further another storage register having an output connected to the second input of the subtractor and another input of the multiplier being connected to the output of the storage memory of said coefficient $\gamma$.

4. Scintillation camera according to claim 3, wherein said multipliers are form a single multiplication circuit means associated with a time multiplexer-demultiplexer for multiplying said signals.

5. Scintillation camera according to claim 1, wherein said event processing stage means includes three unstacking computation circuit means for receiving and delivering signals, two divider means for delivering signals, a time realignment circuit means for receiving an output of one of said unstacking computation circuit means, and an additional computation circuit means for receiving and delivering said signals, said two divider means receiving signals $X_m$, $Y_m$, $Z_m$ in order to deliver two signals $x_m = X_m/Z_m$ and $y_m = Y_m/Z_m$, two of said unstacking computation circuit means receiving said signals $x_m$, $y_m$ and delivering the signals x, y, and a further unstacking computation circuit means receiving the signal $E_m$ and delivering the signal E, and wherein the additional computation circuit receives said signal E and said correction coefficients in order to supply to said two unstacking computation circuit means an additional correction coefficient $\Gamma$.

6. Scintillation camera comprising a scintillator crystal, a matrix of p photodetectors, each providing a respective output signal after conversion of each scintillation into an electric value, p acquisition channels delivering p electrical signals of characteristics of the intensity of the scintillation and of the distance of said scintillation from each of the photo-detectors, and computer means for delivering the coordinates $x_j$ and $y_j$ of a scintillation j and the energy $E_j$ associated with this event j, said scintillation camera further comprising (A) said p acquisition channels including means for amplifying, filtering, and sampling said output signals of the photodetectors, and means for analog-digital converting and summing of signals obtained, said p acquisition channels delivering p digital signals;
(B) transfer control stage means for connecting outputs of said p acquisition channels with said computer means and including means for controlling among the p available signals at the output of said channels the transfer to said computer means of a random number p' of said output signals, said number p' being selected by computation of a threshold $m_{oj}$ related both to the energy and to the stacking effect of detected events, and said transfer control stage means eliminating p-p' signals lower than said threshold;
(C) said computer means further including:
(a) digital summing stage means for receiving said output signals from said transfer control stage means and for delivering the signals $X_{m,j}$, $Y_{m,j}$, where $$X_{m,j} = \sum_{i=1}^{i=p'} K_i (M_{ij} - m_{oj})$$

$$Y_{m,j} = \sum_{i=1}^{i=p'} H_i (M_{ij} - m_{oj})$$

and the digital energy signal $E_{mj}$, where $K_i$, and $H_i$, are weighting coefficients;
(b) event processing stage means for receiving said signals $X_{m,j}$, $Y_{m,j}$, $E_{m,j}$, and for delivering three coordinate and energy signals x, y and E;
(D) detection, sequencing and storage stage means for receiving an analog signal from a summing amplifier, said analog signal corresponding with the sum of the p output signals of the photodetectors, said detection, sequencing and storage stage means delivering various clock signals for synchronization of said p acquisition channels from said transfer control stage means and from said computer means, and said detection, sequencing and storage stage means delivering correction coefficients intended for said event processing stage means; and
(E) said transfer control stage means further including:
(a) p subtractors receiving on a first input a corresponding output of the p acquisition channels and on a second common input said threshold evaluated by a threshold computer;

(b) an additional acquisition channel providing to said threshold computer said digital energy signal $E_{m,j}$ for evaluation of said threshold;

(c) (p+1) transfer control circuits located at the output of said additional acquisition channel and at said p subtractors, the $(p+1)^{th}$ of these circuits providing transfer of the energy signal; and (d) transfer bus means for receiving the (p+1) output signals of said (p+1) transfer control circuits and for delivering to said computer means the energy signal and p' signals from among said p output signals of the p first transfer control circuits.

7. Scintillation camera according to claim 6, wherein said event processing stage means includes three unstacking computation circuit means for respectively receiving said digital signals $X_m$, $Y_m$, $E_m$ and delivering three signals X, Y, E, and two divider means for respectively delivering two signals X=X/E and y=Y/E, said three signals x, y, E being respectively constituted by the output signals of a first of said two divider means, a second of said two divider means and a time realignment circuit means for receiving the output of a last unstacking computation circuit, and wherein said correction coefficients are coefficients for correction by extrapolation and interpolation, $\alpha$ and $\gamma$ respectively, said correction coefficients being intended for the three unstacking computation circuit means of said event processing stage means.

8. Scintillation camera according to claims 2 or 7, wherein each of said three unstacking computation circuit means includes a subtractor receiving on a first input the corresponding output of said digital summation stage means, said subtractor being followed by a first multiplier and by a first storage register, and in parallel with said first multiplier and said first register, by a second multiplier and a second storage register, said second register having an output connected to a second input of said subtractor, and the second inputs of the first and second multipliers being connected first to the input of the storage memory of the coefficient $\alpha$ and secondly to the output of the storage memory of the coefficient $\gamma$.

9. Scintillation camera according to claim 8, wherein the multipliers are a single multiplication circuit means associated with a time multiplexer-demultiplexer for multiplying said signals.

10. Scintillation camera according to claims 2 or 7, wherein each of said unstacking computation circuit means includes a subtractor receiving a first input the corresponding output of said digital summation stage means, said subtractor being followed by a storage register having an output of the corresponding unstacking computation circuit means, and in parallel, another multiplier and storage register having an output connected to a second input of said subtractor and said another multiplier having another input connected to the output of the storage memory of the coefficient $\gamma$.

11. Scintillation camera according to claim 7, wherein said event processing stage means includes three unstacking computation circuit means, two divider means, a timer realignment circuit means, and an additional computation circuit means, said two divider means receiving signals $X_m$, $Y_m$, $E_m$ in order to deliver two signals $X_m = X_m/E_m$ and $y_m = Y_m E_m$, two of said unstacking computation circuit means receiving said signals $x_m$, $y_m$ and delivering signals x, y, and another of said unstacking computation circuits receiving the signal $E_m$ and delivering a signal E, and said additional computation circuit means receiving said signal E and said correction coefficients in order to supply to said two of said unstacking computation circuit means an additional correction coefficient $\Gamma$.

12. Scintillation camera according to claim 1 or 6, wherein the divider means are a single division circuit means associated with a time multiplexer-demultiplexer for dividing said signal.

13. Scintillation camera according to claims 1 or 6, wherein said unstacking computation circuit means are replaced by a single unstacking computation circuit means with which is associated a time multiplexer-demultiplexer.

14. Scintillation camera according to claims 1 or 6, wherein an amplitude rejection circuit means is included for reducing the number of events to be processed.

15. Scintillation camera according to claims 1 or 2, wherein FIFO memories are provided downstream of said p acquisition channels, or upstream of said digital summing stage means.

* * * * *